United States Patent
Ammermann et al.

[11] Patent Number: 5,902,828
[45] Date of Patent: May 11, 1999

[54] FUNGICIDAL MIXTURES

[76] Inventors: Eberhard Ammermann, Heppenheim; Gisela Lorenz, Hambach; Dietrich Mappes, Westheim; Klaus Schelberger, Gönnheim; Manfred Hampel, Neustadt, all of Germany

[21] Appl. No.: 08/750,061
[22] PCT Filed: May 23, 1995
[86] PCT No.: PCT/EP95/01953
  § 371 Date: Dec. 4, 1996
  § 102(e) Date: Dec. 4, 1996
[87] PCT Pub. No.: WO95/34205
  PCT Pub. Date: Dec. 21, 1995

[30] Foreign Application Priority Data

Jun. 10, 1994 [DE] Germany ............... 44202776

[51] Int. Cl.$^6$ ............ A01N 47/10; A01N 37/12; A01N 37/44
[52] U.S. Cl. ............ 514/539; 514/476; 514/491
[58] Field of Search ............ 514/476, 491, 514/539

[56] References Cited

U.S. PATENT DOCUMENTS 4,829,085  5/1989  Wenderoth et al. ............ 514/522

FOREIGN PATENT DOCUMENTS

| | | |
|---|---|---|
| 2 131 854 | 3/1995 | Canada. |
| 254 426 | 1/1988 | European Pat. Off.. |
| 741 970 | 11/1996 | European Pat. Off.. |
| 2 267 644 | 12/1993 | United Kingdom. |
| 2 279 568 | 1/1995 | United Kingdom. |
| 95/15083 | 6/1995 | WIPO. |

OTHER PUBLICATIONS

Chem. Abst. vol. 118, No. 23, Jun. 7, 1993, Abstract No. 228112.
Research Disclosure Nr. 338, 1992 Havant GB, Disclosed Anonymously, Disclosure 33892, Mixtures of Fungicides and Insectcides.

*Primary Examiner*—Allen J. Robinson
*Assistant Examiner*—Alton Pryor

[57] ABSTRACT

A fungicidal mixture comprising
  a) the oxime ether carboxylic ester of the formula I

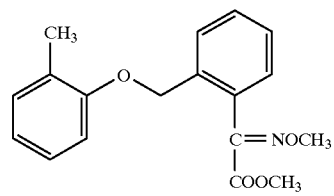

and
  b) a dithiocarbamate (II) selected from the group consisting of
    manganese ethylenebis(dithiocarbamate) (zinc complex) (IIa),
    manganese ethylenebis(dithiocarbamate) (IIb),
    zinc ammoniate ethylenebis(dithiocarbamate) (IIc) and
    zinc ethylenebis(dithiocarbamate) (IId)
in a synergistically effective amount.

13 Claims, No Drawings

FUNGICIDAL MIXTURES

This application is a 371 of PCT/EP95/01953 filed May 23, 1995.

The present invention relates to a fungicidal mixture which comprises a) the oxime ether carboxylic ester of the formula Ia or Ib

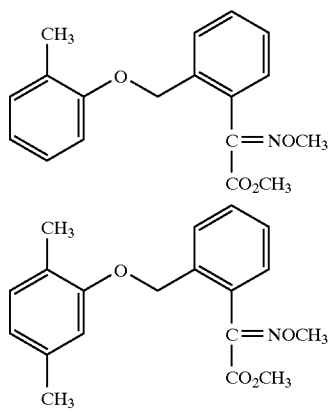

and b) a dithiocarbamate (II) selected from the group consisting of
   - manganese ethylenebis(dithiocarbamate) (zinc complex) (IIa),
   - manganese ethylenebis(dithiocarbamate) (IIb),
   - zinc ammoniate ethylenebis(dithiocarbamate) (IIc) and
   - zinc ethylenebis(dithiocarbamate) (IId)

in a synergistically effective amount.

The present invention also relates to methods for controlling harmful fungi using mixtures of compounds I and II and to the use of compounds I and compounds II for producing mixtures of this type.

The compounds of the formula I (or Ia and Ib), their preparation and their action against harmful fungi is disclosed in the literature (EP-A 253 213).

Likewise known are the dithiocarbamates II (IIa: common name: mancozeb, U.S. Pat. No. 3,379,610; IIb: common name: maneb, U.S. Pat. No. 2,504,404; IIc: former common name: metiram, U.S. Pat. No. 3,248,400; IId: common name: zineb, U.S. Pat. No. 2,457,674), their preparation and their action against harmful fungi.

It is an object of the present invention, with a view to reducing the application rates and improving the spectrum of action of the known compounds, to provide mixtures which have an improved effect on harmful fungi while the total amount of active ingredients applied is reduced (synergistic mixtures).

We have found that this object is achieved by the mixtures defined at the outset. We have also found that harmful fungi can be controlled better on simultaneous conjoint or separate use of the compounds I and compounds II or on use of the compounds I and compounds II successively than with the individual compounds.

The compounds of the formula I can have the E or Z configuration for the C=X double bond (relative to the carboxyl group). Accordingly, they can each be used either as pure E or Z isomer or as E/Z isomer mixture in the mixture according to the invention. The E/Z isomer mixture or the E isomer is preferably used, and the E isomer is particularly preferred.

The pure active ingredients I and II are preferably employed in the preparation of the mixtures, which can as required be admixed with further active ingredients against harmful fungi or other pests such as insects, arachnids or nematodes, or else herbicidal or growth-regulating active ingredients or fertilizers.

The mixtures of compounds I and II and simultaneous conjoint or separate use of the compounds I and II are distinguished by an excellent action against a wide range of phytopathogenic fungi, in particular from the class of Ascomycetes and Basidiomycetes. Some of them have systemic activity and can therefore also be used as foliar and soil fungicides.

They are particularly important for controlling a large number of fungi on a variety of crop plants such as cotton, vegetables (eg. cucumbers, beans and cucurbits), barley, grass, oats, coffee, corn, fruit plants, rice, rye, soybean, grapevines, wheat, ornamental plants, sugar cane and a large number of seeds.

They are particularly suitable for controlling the following phytopathogenic fungi: *Erysiphe graminis* (powdery mildew) on cereals, *Erysiphe cichoracearum* and *Sphaerotheca fuliginea* on curcurbits, *Podosphaera leucotricha* on apples, *Uncinula necator* on vines, Puccinia species on cereals, Rhizoctonia species on cotton and lawns, Ustilago species on cereals and sugar cane, *Venturia inaequalis* (scab) on apples, Helminthosporium species on cereals, *Septoria nodorum* on wheat, *Botrytis cinera* (gray mold) on strawberries and vines, *Cercospora arachidicola* on peanuts, *Pseudocercosporella herpotrichoides* on wheat and barley, *Pyricularia oryzae* on rice, *Phytophthora infestans* on potatoes and tomatoes, *Plasmopara viticola* on vines, Alternaria species on vegetables and fruit and Fusarium and Verticillium species.

They can also be used in material protection (eg. wood protection), for example against *Paecilomyces variotii*.

The compounds I and II can be applied simultaneously, conjointly or separately, or successively, and the sequence of separate application generally has no effect on the result of control.

The compounds I and II are normally used in a ratio by weight of from 50:1 to 2:1, preferably 40:1 to 1.8:1, in particular 30:1 to 1.8:1 (II:I).

The application rates of the mixtures according to the invention depend on the nature of the desired effect and are from 0.005 to 0.5 kg/ha, preferably 0.01 to 0.5 kg/ha, in particular 0.01 to 0.3 kg/ha, for compounds I. The application rates for compounds II are correspondingly from 0.1 to 10 kg/ha, preferably 0.5 to 5 kg/ha, in particular 1 to 4 kg/ha.

The application rates of the mixture for seed treatment are generally from 0.001 to 100 g/kg of seeds, preferably 0.01 to 50 g/kg, in particular 0.01 to 10 g/kg.

Where harmful fungi which are pathogenic for plants are to be controlled, the separate or conjoint application of the compounds I and II or of the mixtures of compounds I and II takes place by spraying or dusting the seeds, the plants or the soil before or after sowing the plants or before or after emergence of the plants.

The fungicidal synergistic mixtures according to the invention, or the compounds I and II can be prepared, for example, in the form of directly sprayable solutions, powders and suspensions or in the form of high-percentage aqueous, oily or other suspensions, dispersions, emulsions, oil dispersions, pastes, dusting agents, scattering agents or granules, and be used by spraying, atomizing, dusting, scattering or pouring. The application form depends on the purpose of use; it should in every case ensure dispersion of the mixture according to the invention which is as fine and uniform as possible.

The formulations are produced in a conventional way, eg. by adding solvents and/or carriers. Inert additives such as emulsifiers or dispersants are normally mixed with the formulations.

Suitable surface-active substances are the alkali metal, alkaline earth metal and ammonium salts of aromatic sulfonic acids, eg. lignin-, phenol-, naphthalene- and dibutyl-naphthalenesulfonic acid, and of fatty acids, alkyl- and alkylarylsulfonates, alkyl, lauryl ether and fatty alcohol sulfates, and salts of sulfated hexa-, hepta- and octadecanols or fatty alcohol glycol ethers, condensation products of sulfonated naphthalene and its derivatives with formaldehyde, condensation products of naphthalene or of naphthalenesulfonic acids with phenol and formaldehyde, polyoxyethylene octylphenol ethers, ethoxylated isooctyl-, octyl- or nonylphenol, alkylphenol or tributylphenyl polyglycol ether, alkylaryl polyether alkohols, isotridecyl alcohol, fatty alcohol ethylene oxide condensates, ethoxylated castor oil, polyoxyethylene alkyl ethers or polyoxypropylene, lauryl alcohol polyglycol ether acetate, sorbitol esters, lignin sulfite waste liquors or methylcellulose.

Scattering and dusting powders can be produced by mixing or milling together the compounds I or II or the mixture of compounds I and II with a solid carrier.

Granules (eg. coated, impregnated or homogenous granules) are normally produced by binding the active ingredient or ingredients on a solid carrier.

Examples of fillers and solid carriers which are used are mineral earths such as silica gel, silicas, silica gels, silicates, talc, kaolin, limestone, lime, chalk, bole, loess, clay, dolomite, diatomaceous earth, calcium sulfate, magnesium sulfate, magnesium oxide, ground plastics, and fertilizers such as ammonium sulfate, ammonium phosphate, ammonium nitrate, ureas and vegetable products such as cereal flour, bark meal, wood meal and nutshell meal, cellulose powder or other solid carriers.

The formulations generally contain from 0.1 to 95% by weight, preferably 0.5 to 90% by weight, of one of the compounds I or II or the mixture of compounds I and II. The active ingredients are employed for this purpose in a purity of from 90% to 100%, preferably 95% to 100% (according to NMR or HPLC spectrum).

The compounds I or II or the mixtures or the corresponding formulations are used by treating the harmful fungi, or the plants, seeds, soil, areas, materials or rooms which are to be kept free of them with a fungicidally effective amount of the mixture or of the compounds I and II on separate application. The use can take place before or after attack by the harmful fungi.

Examples of the synergistic effect of the mixtures according to the invention against harmful fungi.

The fungicidal action of the compounds and of the mixtures was shown by the following test:

The active ingredients were prepared separately or conjointly as 20% strength emulsion in a mixture of 70% by weight of cyclohexanone, 20% by weight of Nekanil® LN (Lutensol® AP6, wetting agent with emulsifying and dispersing action based on ethoxylated alkylphenols) and 10% by weight of Emulphor® EL (Emulan® EL, emulsifier based on ethoxylated fatty alcohols) and diluted to the required concentration with water.

Evaluation took place by establishing the percentage of leaf area attacked. These percentages were converted into efficacies. The efficacies to be expected for the active ingredient mixtures were determined by the Colby formula [R. S. Colby, Weeds 15, 20–22 (1967)] and compared with the observed efficacies.

Colby formula:

$$E = x + y - x \cdot y / 100$$

E efficacy to be expected, expressed as % of untreated control on use of the mixture of active ingredients A and B in concentrations a and b x the efficacy expressed as % of the untreated control on use of active ingredient A in concentration a y the efficacy expressed as % of the untreated control on use of active ingredient B in concentration b An efficacy of 0 means that the attack on the treated plants corresponds to that on the untreated control plants; an efficacy of 100 means that the treated plants show no attack.

A. Efficacy against Plasmopara viticola (vine peronospora)

Pot vines (variety: Müller Thurgau) were sprayed to run-off with the active ingredient preparation. After 8 days, the plants were sprayed with a suspension of zoospores of the fungus *Plasmopara viticola* and initially stored at 24° C. and 100% humidity for 48 h. The test plants were then left in a glasshouse at 20–30° C. for 5 days. Before the assessment, the plants were stored at high humidity for a further 16 h. The evaluation took place by inspection of the undersides of the leaves.

| Active ingredient | Application rate [ppm] | Efficacy [%] |
|---|---|---|
| —/—* | — | 0 |
| Ia | 31 | 48 |
| Ia | 8 | 0 |
| IIc | 310 | 80 |
| IIc | 80 | 48 |

| Mixture [application rate] | Efficacy [observed] | Efficacy [calculated] |
|---|---|---|
| Ia + IIc 31 + 310 | 100 | 90 |
| Ia + IIc 8 + 80 | 95 | 48 |

*77% attack of untreated control

B: Efficacy against Phytophthora infestans (late blight)

Leaves of tomato plants (variety: Große Fleischtomate) were initially treated with the aqueous preparation of the active ingredients. After about 48 h, the plants were infected with a suspension of zoospores of *Phytophthora infestans*. The plants treated in this way were then incubated at 16–18° C. and a relative humidity of 100% for 6 days. The extent of fungal development was then determined.

| Active ingredient | Application rate [ppm] | Efficacy [%] |
|---|---|---|
| —/—* | — | 0 |
| Ia | 8 | 70 |
| Ia | 4 | 40 |
| IIc | 80 | 85 |
| IIc | 40 | 79 |

| Mixture [application rate] | Efficacy [observed] | Efficacy [calculated] |
|---|---|---|
| Ia + IIc 8 + 80 | 100 | 95 |
| Ia + IIc 4 + 40 | 94 | 88 |

*34% attack of untreated control

We claim:
1. A fungicidal mixture comprising
a) the oxime ether carboxylic ester of the formula Ia or Ib

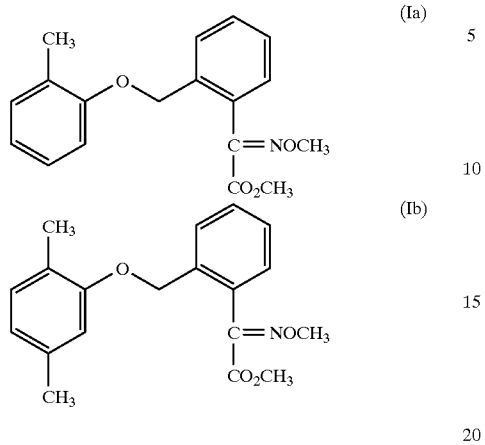

and
b) a dithiocarbamate (II) selected from the group consisting of
manganese ethylenebis(dithiocarbamate) (zinc complex) (IIa),
manganese ethylenebis(dithiocarbamate) (IIb),
zinc ammoniate ethylenebis(dithiocarbamate) (IIc), and
zinc ethylenebis(dithiocarbamate) (IId)
in a synergistically effective amount.

2. The fungicidal mixture of claim 1, wherein b) is manganese ethylenebis(dithiocarbamate) (IIb).

3. The fungicidal mixture of claim 1, wherein the weight ratio of the dithiocarbamate (II) to the oxime ether carboxylic ester of the formula Ia or Ib is from 50:1 to 2:1.

4. A method of controlling harmful fungi, which comprises treating the harmful fungi, their habitat or the plants, seeds, soil, areas or materials to be kept free of said fungi with synergistically effective amounts of a oxime ether carboxylic ester of the formula Ia or Ib as defined in claim 1 and a dithiocarbamate (II) as defined in claim 1.

5. The method of claim 4, wherein the oxime ether carboxylic ester of the formula Ia or Ib and the dithiocarbamate (II) are applied simultaneously or separately.

6. The method of claim 4, wherein from 0.005 to 0.5 kg/ha of the oxime ether carboxylic ester of the formula Ia or Ib is applied.

7. The method of claim 4, wherein from 0.1 to 10 kg/ha of the dithiocarbamate (II) is applied.

8. A fungicidal mixture comprising
a) the oxime ether carboxylic ester of the formula Ia

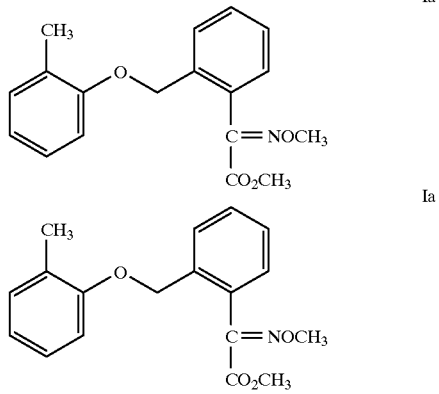

and
b) zinc ammoniate ethylenebis(dithiocarbamate) (IIc)
in a synergistically effective amount.

9. A fungicidal mixture as claimed in claim 1, wherein the ratio by weight of compound II(c) to compound I(a) is from 50:1 to 2:1.

10. A method for controlling harmful fungi, which comprises treating the harmful fungi, their habitat or the plants, seeds, soil, areas or materials to be kept free of said fungi with synergistically effective amounts of a compound of the formula Ia as defined in claim 1 and the compound IIc as defined in claim 1.

11. The method of claim 10, wherein the compound of the formula Ia and the compound IIc are applied together or separately or successively.

12. The method of claim 10, wherein from 0.005 to 0.5 kg/ha of the compound of the formula Ia is applied.

13. The method of claim 10, wherein from 0.1 to 10 kg/ha of the compound IIc is applied.

* * * * *

UNITED STATES PATENT AND TRADEMARK OFFICE
CERTIFICATE OF CORRECTION

PATENT NO. : 5,902,828
DATED : May 11, 1999
INVENTOR(S) : Ammermann, et al

It is certified that error appears in the above-identified patent and that said Letters Patent is hereby corrected as shown below:

Col. 6, claim 8, after line 5, delete one of the formula Ia, which is shown in duplicate.

Col. 6, claim 9, line 27, "claim 1" should be --claim 8--.

Col. 6, claim 10, line 35, "claim 1" should be --claim 8--.

Signed and Sealed this

Seventh Day of September, 1999

Attest:

Q. TODD DICKINSON

Attesting Officer

Acting Commissioner of Patents and Trademarks